United States Patent [19]

Roll

[11] 4,310,532
[45] Jan. 12, 1982

[54] METHODS AND PIPERIDINYL-ALKYL-BENZAMIDE COMPOSITION FOR INHIBITING $H_2$ HISTAMINE RECEPTORS

[75] Inventor: William D. Roll, Toledo, Ohio

[73] Assignee: The University of Toledo, Toledo, Ohio

[21] Appl. No.: 133,453

[22] Filed: Mar. 24, 1980

[51] Int. Cl.³ .......................................... A61K 31/445
[52] U.S. Cl. ................................................. 424/267
[58] Field of Search ........................................ 424/267

[56] References Cited

U.S. PATENT DOCUMENTS 3,936,468  2/1976  Yamamoto et al. ............... 424/267

Primary Examiner—Frederick E. Waddell

Attorney, Agent, or Firm—Wilson, Fraser, Barker & Clemens

[57] ABSTRACT

Pharmaceutical compositions for the treatment of ulcerative disorders comprising therapeutically effective amounts of compounds of the formula:

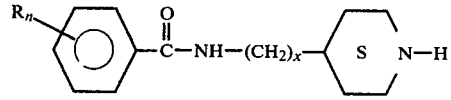

wherein R is hydrogen, an alkyl group having from 1 to 4 carbon atoms, an alkoxy group having from 1 to 4 carbon atoms, halo, amino, hydroxy, or where R is meta trifluoromethyl, n is 1, 2, or 3 when R is methoxy, but is otherwise 1, and x is 1, 2, or 3, with the proviso that when n is 1, R in the meta position is trifluoromethyl or hydrogen, and physiologically acceptable salts thereof.

11 Claims, No Drawings

METHODS AND PIPERIDINYL-ALKYL-BENZAMIDE COMPOSITION FOR INHIBITING H2 HISTAMINE RECEPTORS

BACKGROUND OF THE INVENTION

Similarly structured piperidinyl-alkyl-benzamides have not heretofore been found to be therapeutically effective in the management of ulcerative disorders affecting the gastrointestinal system. Mepyramine is a prototype for compounds which have histamine $H_1$ antagonism activity and which are commonly referred to as antihistamines; whereas burimamide and metiamide have been identified as histamine $H_2$ antagonist prototypes. Black et al. related the invention of pharmaceutical compositions having both $H_1$ and $H_2$ bioreceptor inhibiting activity for use as anti-inflammatory agents and as cardiovascular agents wherein upsets are associated with high levels of histamine in U.S. Pat. No. 3,894,151. This culminated in the introduction of cimetidine as the initial clinically useful histamine $H_2$ antagonist drug. In an extension of this work we have evaluated a series of piperidinyl-alkyl-benzamide structures and salts thereof for their histamine $H_1$- and $H_2$-antagonism activity.

SUMMARY OF THE INVENTION

This invention comprises pharmaceutical compositions containing various benzamides having $H_2$ antagonism (anti-ulcer) activity and methods of administering these compositions to small animals to produce this effect.

DESCRIPTION OF THE PREFERRED EMBODIMENT

The compositions of this invention are unit dosage forms, such as tablet or sterile solution for injection, containing a therapeutically effective amount of piperidinyl-alkyl-benzamide having the general formula:

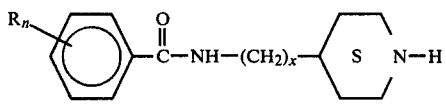

wherein R is hydrogen, an alkyl group having from 1 to 4 carbon atoms, an alkoxy group having from 1 to 4 carbon atoms, halo, amino, hydroxy, or where R is metatrifluoromethyl, n is 1, 2, or 3 when R is methoxy, but is otherwise 1, and x is 1, 2, or 3 with the proviso that when n is 1, R in the meta position is trifluoromethyl or hydrogen and physiologically acceptable salts thereof.

The compounds were prepared by interacting a series of substituted benzoyl halides with equimolar amounts of 4-pyridyl-alkyl-amines in the presence of triethylamine in anhydrous chloroform. The resultant N-(4-pryidyl-alkyl)-benzamide products were converted to their corresponding piperidine analogs by catalytic hydrogenation using 10% Pd/C in an acidic ethanol solvent system using an initial pressure 68 psi $H_2$ at a temperature of 60°-70° C. The reaction was generally complete after approximately five hours. The piperidinyl-alkyl-benzamide products were commonly recrystallized from isopropanol given pure products in yields ranging from 66-89%.

The synthetic pathway is shown below:

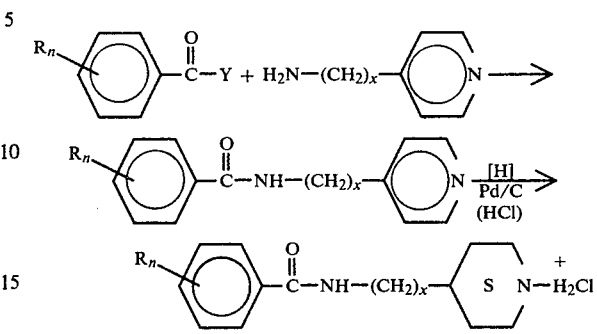

The histamine $H_2$ antagonism activity of these piperidinyl-alkyl-benzamide compounds was tested on the isolated guinea pig atrium. The atria from Hartley strain guinea pigs were dissected and suspended in 25 ml of McEwen's solution and attached to a transducer. Spontaneous atrial rate was determined from the recorder tracing. Chronotropic responses to increasing concentrations of histamine (0.05–2.5 μg/ml) were evaluated in the presence of placebo or experimental compound. Results are expressed in Table I as the ratio of concentration of histamine required to increase atrial rate by 50 beats/minute:concentration of histamine required to increase atrial rate by 50 beats/minute in the presence of experimental compound, 10 μg/ml.

TABLE I

| COMPOUND | HISTAMINE RATIO |
|---|---|
| $\bigcirc$—C(=O)—NH—CH$_2$—(S $\overset{+}{N}$H$_2$Cl$^-$) | 0.005 |
| CH$_3$—$\bigcirc$—C(=O)—NH—CH$_2$—(S $\overset{+}{N}$H$_2$Cl$^-$) | 0.004 |
| Cimetidine | 0.0025 |

The piperidine-alkyl-benzamides, as their hydrochloride salts, were evaluated for histamine $H_2$ antagonist activity, in vivo, by their ability to block the stimulation of acid secretion by histamine from the lumen-perfused anesthetized (urethane) rat preparation as described in Ash and Shield, Br. J. Pharmacol. Chemotherapy 27, 427 (1966) and Durant, et al., J. Med. Chem. 18, 905 (1975). Sprague Dawley rats weighing between 150-200 g were used for the evaluations. Perfusion was carried out with 5% glucose solution at 37° C. Administration of histamine and test compounds was carried out by rapid I.V. injection via cannulated jugular vein. Doses of 0.13 μmol/kg/hr. of histamine were used, and 0.24 mg/kg of antagonist test compound. The results are detailed in Table II.

TABLE II

| COMPOUND | MEAN % INHIBITION OF GASTRIC ACID SECRETION |
|---|---|
| $\bigcirc$—C(=O)—NH—CH$_2$—(S $\overset{+}{N}$H$_2$Cl$^-$) | 40 ± 6 |

TABLE II-continued

| COMPOUND | MEAN % INHIBITION OF GASTRIC ACID SECRETION |
|---|---|
| CH$_3$—⟨O⟩—C(=O)—NH—CH$_2$—⟨S⁺ NH$_2$Cl⁻⟩ | 52 ± 5 |
| Cimetidine | 78 ± 8 |

Further evaluation involved testing the ability of the piperidinyl-alkyl-benzamides to block the response to histamine by the isolated rat uterus. Female Sprague Dawley rats weighing approximately 150 g were injected with diethylstilbesterol (0.15 mg/rat) fifteen hours prior to sacrifice. Single uterine horns were placed in 25 ml of Locke Ringers solution (34° C., 95% $O_2$–5% $CO_2$). Contractile responses were evaluated after the addition of placebo; after the addition of experimental compounds; and after the addition of histamine (25 μg/ml). The results are expressed as the % change in the contractile response to histamine relative to placebo-histamine evaluation in Table III. ($EC_{50}$=the concentration in μg/ml of experimental compound required to block the contractile effect of histamine by 50%).

TABLE III

| COMPOUND | $EC_{50}$, μg/ml |
|---|---|
| ⟨O⟩—C(=O)—NH—CH$_2$—⟨S⁺ NH$_2$Cl⁻⟩ | 0.38 |
| CH$_3$—⟨O⟩—C(=O)—NH—CH$_2$—⟨S⁺ NH$_2$Cl⁻⟩ | 0.31 |
| Cimetidine | 0.30 |

EXAMPLE 1

N-(4-Piperidinylmethyl)benzamide was synthesized by the dropwise addition of 0.12 mole benzoyl chloride to a mixture composed of 0.12 mole 4-pyridylmethylamine and 0.122 mole triethylamine in 75 ml. dry chloroform with constant stirring over a period of 30 minutes. The contents of the reaction vessel were maintained at 10°–15° C. throughout the addition of the benzoyl chloride and for a period of thirty minutes thereafter. Triethylamine hydrochloride, which formed during the course of the reaction, was removed by filtration and the remaining filtrate evacuated in vacuo to yield the crude N-(4-pyridylmethyl)benzamide intermediate. The crude product was recrystallized from aqueous alcohol to give pure product, melting point 176.7° C., 80.5% yield.

The intermediate pure compound, 0.04 mole, was dissolved in 65 ml. of absolute ethanol containing 0.041 mole HCl and 1.1 g. 10% Pd/C and reduced at a temperature of 60°–70° C. at 68 psi for about five hours. The catalyst was removed by filtration, and the filtrate evacuated in vacuo to give the crude product, N-(4-piperidinylmethyl)benzamide. The pure product was obtained following recrystallization from isopropanol, melting point 119° C., 73.6% yield.

The product was evaluated according to Tables I, II, and III above. This compound showed a significant amount of histamine $H_2$—receptor antagonist activity in standard pharmacological tests.

EXAMPLE 2

N-(4-pyridylmethyl)-p-methylbenzamide was synthesized from p-toluoyl chloride and 4-pryidylmethylamine in the same manner as employed in Example 1 above. The pure product has a melting point 142.7° C., yield of 87.7%. The intermediate product was converted to pure N-(4-piperidinylmethyl)-p-methylbenzamide as previously described (Example 1); melting point 226.6° C., yield 70.7%, and evaluated according to Tables I, II, and III.

EXAMPLE 3

| Tablet Formulation | Gm./Tablet |
|---|---|
| Test Compound | 0.300 |
| Lactose | 0.400 |
| Sucrose | 0.056 |
| Corn Starch | 0.008 |
| Stearic Acid | 0.036 |

The ingredients of the formulation are granulated and compressed by standard pharmaceutical procedures.

EXAMPLE 4

| Parenteral Formulation (for intravenous) or intramuscular injection) | |
|---|---|
| Test Compound | 20.0% |
| Phenol | 0.5% |
| Water for injection, USP, qsad | 100.0% |

The above Examples (3 and 4) are made only by way of example and are not intended to limit the scope of this invention.

I claim:

1. The method of inhibiting $H_2$ histamine receptors comprising the steps of:
   (A) preparing a unit dosage of an amount sufficient to inhibit $H_2$ histamine receptors of piperidinyl-alkyl-benzamide having the general formula:

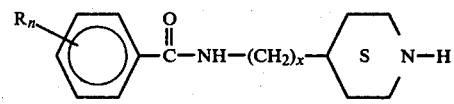

wherein R is hydrogen, an alkyl group having from 1 to 4 carbon atoms, an alkoxy group having from 1 to 4 carbon atoms, halo, amino, hydroxy, or where R is meta trifluoromethyl, n is 1, 2, or 3 when R is methoxy, but is otherwise 1, and x is 1, 2, or 3 with the proviso that when n is 1, R in the meta position is trifluoromethyl or hydrogen and physiologically acceptable salts thereof;
   (B) administering an amount sufficient to inhibit $H_2$ histamine receptors of said piperidinyl-alkyl-benzamide to an animal requiring inhibition of said $H_2$ histamine receptors.

2. The method of inhibiting $H_2$ histamine receptors comprising the steps of:
   (A) granulating and compressing in a tablet the following ingredients in proportion:

| | | Gm/Tablet |
|---|---|---|
| (a) | a piperidinyl-alkyl-benzamide having the general formula: | .300 |

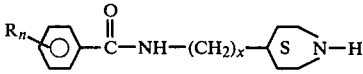

wherein R is hydrogen, an alkyl group having from 1 to 4 carbon atoms, an alkoxy group having from 1 to 4 carbon atoms, halo, amino, hydroxy, or where R is meta trifluoromethyl, n is 1, 2, or 3 when R is methoxy, but is otherwise 1, and x is 1, 2, or 3 with the proviso that when n is 1, R in the meta position is trifluoromethyl or hydrogen and physiologically acceptable salts thereof;

| (b) | lactose | .400 |
|---|---|---|
| (c) | sucrose | .056 |
| (d) | corn starch | .008 |
| (e) | stearic acid | .036 |

(B) administering said tablet to an animal requiring inhibition of said $H_2$ histamine receptors.

3. The method of inhibiting $H_2$ histamine receptors comprising the steps of:
(A) combining the following ingredients in a parenteral formulation:

| (a) | a piperidinyl-alkyl-benzamide having the general formula: | 20.0% |
|---|---|---|

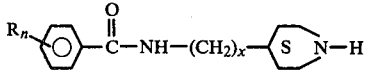

where R is hydrogen, an alkyl group having from 1 to 4 carbon atoms, an alkoxy group having from 1 to 4 carbon atoms, halo, amino, hydroxy, or where R is meta trifluoromethyl, n is 1, 2, or 3 when R is methoxy, but is otherwise 1, and x is 1, 2, or 3 when the proviso that when n is 1, R in the meta position is trifluoromethyl or hydrogen and physiologically acceptable salts thereof.

| (b) | phenol | .05% |
|---|---|---|
| (c) | water for injection, USP, qsad | 100.0% |

(B) administering said parenteral formulation to an animal requiring inhibition of said $H_2$ histamine receptors.

4. The method of inhibiting $H_2$ histamine receptors as described in claim 3 wherein the application of said parenteral formulation is by intravenous injection.

5. The method of inhibiting $H_2$ histamine receptors as described in claim 3 wherein the administration of said parenteral formulation is by intramuscular injection.

6. The method of inhibiting $H_2$ histamine receptors as described in claim 2 wherein the administration of said tablet is orally.

7. The method of inhibiting $H_2$ histamine receptors as described in claim 2 or 3 wherein the piperidinyl-alkyl-benzamide has the formula:

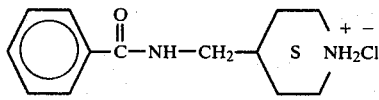

8. The method of inhibiting $H_2$ histamine receptors as described in claims 2 or 3 wherein the piperidinyl-alkyl-benzamide has the formula:

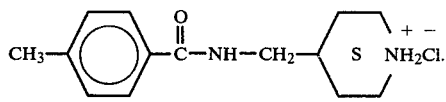

9. Pharmaceutical compositions which inhibit $H_2$ histamine receptors for the treatment of animals requiring inhibition of said $H_2$ histamine receptors comprising a filler and a therapeutically effective amount of a piperidinyl-alkyl-benzamide having the general formula:

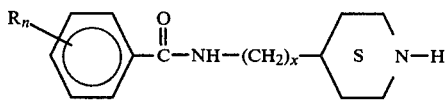

wherein R is hydrogen, an alkyl group having from 1 to 4 carbon atoms, an alkoxy group having from 1 to 4 carbon atoms, halo, amino, hydroxy, or where R is meta trifluoromethyl, n is 1, 2, or 3 when R is methoxy, but is otherwise 1, and x is 1, 2, or 3 with the proviso that when n is 1, R in the meta position is trifluoromethyl or hydrogen and physiologically acceptable salts thereof.

10. Pharmaceutical compositions which inhibit $H_2$ histamine receptors in the form of a tablet for the treatment of an animal requiring inhibition of said $H_2$ histamine receptors comprising:

| | | Gm/Tablet |
|---|---|---|
| (A) | piperidinyl-alkyl-benzamide having the general formula: | 0.300 |

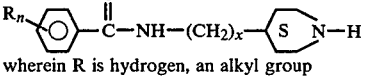

wherein R is hydrogen, an alkyl group having from 1 to 4 carbon atoms, an alkoxy group having from 1 to 4 carbon atoms, halo, amino, hydroxy, or where R is meta trifluoromethyl, n is 1, 2 or 3 when R is methoxy, but is otherwise 1, and x is 1, 2 or 3 with the proviso that when n is 1, R in the meta position is trifluoromethyl or hydrogen and physiologically acceptable salts thereof;

| (B) | Lactose | 0.400 |
|---|---|---|
| (C) | Sucrose | 0.056 |
| (D) | Corn Starch | 0.008 |
| (E) | Stearic Acid | 0.036 |

11. Pharmaceutical compositions which inhibit $H_2$ histamine receptors in the form of parenteral formulations for the treatment of an animal requiring inhibition of said $H_2$ histamine receptors comprising:

| (A) | piperidinyl-alkyl-benzamide having the general formula: | 20.0% |
|---|---|---|

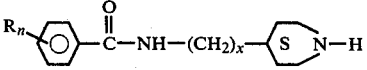

wherein R is hydrogen, an alkyl group having from 1 to 4 carbon atoms, an alkoxy group having from 1 to 4 carbon atoms, halo, amino, hydroxy, or where R is meta trifluoromethyl, n is 1, 2, or 3 when R is methoxy, but is otherwise 1, and x is 1, 2, or 3 with the proviso that when n is 1, R in the meta position is trifluoromethyl or hydrogen and physiologically acceptable salts thereof

| (B) | phenol | 6.5% |
|---|---|---|
| (C) | water for injection, USP, qsad | 100.0% |

* * * * *